United States Patent [19]

Negri et al.

[11] Patent Number: 5,066,232
[45] Date of Patent: Nov. 19, 1991

[54] METHOD OF REMOVING PULP WITH AN ALKALINE PRODUCT

[75] Inventors: Febo R. Negri, Milan; Ercole Tomasini, Mirandola, both of Italy

[73] Assignee: Biomedic S.r.l., Milan, Italy

[21] Appl. No.: 592,947

[22] Filed: Oct. 4, 1990

[30] Foreign Application Priority Data

Oct. 4, 1989 [IT] Italy ................................ 21917 A/89

[51] Int. Cl.$^5$ ................................................ A61C 5/02
[52] U.S. Cl. ................................................ 433/224
[58] Field of Search ................................ 433/224, 229

[56] References Cited

U.S. PATENT DOCUMENTS

| 3,704,520 | 12/1972 | Weissman | 433/224 |
| 3,871,099 | 3/1975 | Kahn | 433/224 |
| 4,121,940 | 10/1978 | Michel et al. | 433/224 |
| 4,135,302 | 1/1979 | Kronman et al. | 433/102 |
| 4,944,678 | 7/1990 | Villette | 433/224 |

Primary Examiner—John J. Wilson
Assistant Examiner—C. Cherichetti
Attorney, Agent, or Firm—Diller, Ramik & Wight

[57] ABSTRACT

An alkaline product destined to be used in odontiatria for the chemical removal of dentinal pulp in the devitalization operation, the so-said "root canal cure".

10 Claims, No Drawings

METHOD OF REMOVING PULP WITH AN ALKALINE PRODUCT

BACKGROUND OF THE INVENTION

The present invention is concerned with an alkaline product, in particular, but not exclusively, potassium hydroxide, destined to be used in odontiatria for the chemical removal of dentinal pulp in the devitalization operation, commonly called "root canal cure" by those skilled in the art.

During past years, dental surgeons changed their operating philosophy from an eminently demolishing one into one preservative and curative of dental structures. This is because of the greater attention paid to the biomechanical characteristics of mastication which caused people to ackowledge that the chewing load is too high to be supported without damage by the bone structures of gums only. Implantology has often solved the problem of the lack of dental structure but, although it represents a considerable progress, implantology cannot do better then physiologic structures, even if mutilated, and "dead" from a biological viewpoint. So, even a tooth stump, or an isolated root, became invaluable as anchoring points for prostheses which should reproduce the "normal" anatomicofunctional situation as closely as possible.

The most important among the problems deriving from the choice of the preservative treatments is the problem of the removal, which should be as complete as possible, of the tissues left by the inflammatory/flogistic state which led the patient to the dental surgeon. In fact, only in that way the structure of the concerned tooth—or of tooth residues—can be safeguarded over time. The whole preservative treatment rests hence on a perfectly carried out tooth canal cure. Therefore, the essential importance is self-explanatory, namely the prevention of the repetition of pathologic events due to infected residue which were not properly removed in due time.

The mechanical means adopted heretofore for the root canal cure are by now "classic" components of odontiatric instruments: drill, cutters, stylets, nerve extractors. All of these instruments share the need of a considerable tecnical capability, supported by an uncommon "natural" skill of the operator. Therefore, it is not surprising that the number of odontologists who are capable of carrying out a conservative canal cure with good probabilities of success is rather small. The same variability of root canal reduces the possibilities of a really effective treatment. It is enough to think of the impossibility of reaching undercuts or side branchings of a root by means of a straight instrument, in order to realize the difficulties which have to be overcome through instrument techniques.

In short, what the prior art proposes, is performing root canal cures by means of such mechanical means as drills, cutters, and the like, in order to remove root pulp tissues without that the latter having been submitted to any preliminary chemical treatments.

The use of these instruments also implies a painful mechanical action on the concerned part, in order to open and ream the root canal in order to be able to devitalize the tooth by means of the removal—still by means of mechanical instruments—of the nerve.

The so devitalized tooth must be submitted then to a series of treatments, during the course of a certain number of sittings, spaced in time, which should only be carried out by very qualified and skilled people in order to prevent possible residues of pulp tissues, not duly removed, from giving rise to centres of infection or necrosis with abscesses or granulomas consequently occurring.

Therefore, such an operating system is very expensive and a perfect outcome thereof is always subordinated to the capability, skill and professionalism of the operators.

In the search for an alternative method, those skilled in the art had already thought of the possibility that a liquid, fed to the interior of the pulp shell, may reach the otherwise inaccessible points. In fact, solutions of various substances have been long used in odontiatria for the purpose of obtaining a reasonable hope of a successful outcome of even mechanically difficult root canal cures.

For example, such solutions are the solution of sodium hydroxide or sodium carbonate, at concentrations of about 5-10%, used seldom, for fear that it is excessively caustic; organic mixtures which perform a solvent/dehydrating action (e.g., acetone+ether+isopropyl alcohol), also used in order to dry the root canal; solution at 3% or 5% Chloramine T; solution at 17% of EDTA as trisodium salt (generated in solution from diNa EDTA+sodium hydroxide); sodium hypochlorite solution at 5.25%; and hydrogen peroxide solution at a concentration of from 3 to 5% by weight. All of these solutions have been boasted of being capable of dissolving tooth pulp. Actually, what is secured is the mummification of tissues, and their chemical sterilization, while the removal action is still entrusted to the manual skill of the operator. Tests carried out in vitro on a tissue obtained from butchery wastes have confirmed the above statements. In fact, the above cited solutions, and their mixtures, were tested, with uncertain results, and in no case was the assured pulp demolition achieved. Further experiences in vitro, also submitted to statistic analysis in order to verify the reliability and the possible correlation of the results, have confirmed that which had already been intuitively concluded on the basis of the preceding test series. In particular, the solution of Chloramine T (sodium p-toluenesulfonchloramide) and the solution of EDTA at 17%—which is capable of softening dentine by substracting calcium ions from it, but shows to be ineffective versus pulp tissues—showed to be very disappointing, as regards their specific use in odontiatria.

Further studies carried out on pulp nature which evidence the poor effectiveness of alkaline (sodium hydroxide and sodium carbonate) solutions caused researchers to focus their attention on the nature of the fatty acids contained in pulp, which generally are long-chain acids (chain length longer than $C_{16}$). The explanation of the poor effectiveness had hence to be seen in the relatively low saponifying power of sodium alkalies and in the poor solubility of the soaps formed in the reaction, besides a considerable resistance of the proteinic matrix to undergo degradation, but under drastic conditions, decidedly unproposable in an intervention on a patient (high temperatures, times of the order of several hours).

SUMMARY OF THE INVENTION

The general purpose of the present invention is to overcome the drawbacks of prior art chemical root canal techniques, such that the root canal cure or treatment can be performed within times on the order of a few minutes, under aseptic conditions and, above all, without the use of mechanical instruments in order to remove the nerve and possible infected parts from treated region.

Another purpose of the present invention is that of providing an intervention modality by means of which, after the preparation step (opening of pulp cavity and insertion of an insert), the treatment can be continued by paramedical staff.

In order to achieve the above cited purposes, during the systematic search for an alternative, the present applicants surprisingly found that potassium hydroxide, even at other than high concentrations, is capable of meeting in an exceptionally satisfying way the needs of dissolution of tooth pulp and of tissues very different from one another, such as lipoids and correlated tissues, and the proteinic matrix.

The following compositions are set forth for exemplifying purposes, which in no way should be construed and being limitative of the scope of protection of the product which constitutes the subject-matter of the instant invention.

COMPOSITION 1

| 1) Potassium hydroxide, reagent grade | 14.5 g |
| --- | --- |
| 2) Deionized water | q.s. to 100 ml |

The solution should be suitably filtered after preparation. The applicants recommend that the product be packaged inside high-density polyethylene containers.

COMPOSITION 2

| 1) Potassium hydroxide, reagent grade | 20.0 g |
| --- | --- |
| 2) Deionized water | q.s. to 100 ml |

The solution should be suitably filtered after preparation. The applicants recommend that the product be packaged inside high-density polyethylene containers.

COMPOSITION 3

| 1) Potassium hydroxide, reagent grade | 20.0 g |
| --- | --- |
| 2) Nonylphenol/10 mols EO adduct | 0.5 g |
| 3) Deionized water | q.s. to 100 ml |

(EO = ethylene oxide)

The solution should be suitably filtered after preparation. The applicants recommend that the product be packaged inside high-density polyethylene containers.

COMPOSITION 4

| 1) Potassium hydroxide, reagent grade | 20.0 g |
| --- | --- |
| 2) Fluorad FC 430 (non-ionic fluorocompound) | 0.05 g |
| 3) Deionized water | q.s. to 100 ml |

The solution should be suitably filtered after preparation. The applicants recommend that the product be packaged inside high-density polyethylene containers.

For comparison purposes, the values are reported, which were obtained from tests carried out with "classic" solutions—all of which were however unable to completely digest the test sample, of about 500 mg of test tissue—and potassium hydroxide:

| Substance in solution | Concentration | Time (min) |
| --- | --- | --- |
| Potassium hydroxide | 20% | 7 min 30 sec |
| Sodium hydroxide | 50% | 15 minutes |
| Sodium dichloroisocyanurate | 10% | 10 min 20 sec |
| Urea peroxide | 10% (as $H_2O_2$) | 11 min 20 sec |
| Chloramine T | 5% | >12 minutes |
| EDTA | 17% | >15 minutes |
| | pH = about 9 | |

The reported values are the arithmetic average of at least three tests for each solution, with an error of ±15 seconds; the temperature was kept at 35±2° C., assuming that these are the normal conditions for teeth when one person's mouth is opened.

When urea peroxide solution (equivalent to a 12-volume hydrogen peroxide solution) and, to a minor extent, dichloroisocyanurate and Chloramine T solutions, were used, rather than a true dissolution of the sample, a mummification thereof was obtained; and increases in concentration led to a faster mummification, rather than to an oxidation. The only solution capable of causing the sample to be completely colliquated is potassium hydroxide solution.

The statistic analysis of achieved results did not show significant differences between isocyanurate, Chloramine T and hydrogen peroxide solutions; in the same way, EDTA solution—which can find an application in all those cases which do not involve pulp removal—has to be regarded as lacking effectiveness, and sodium hydroxide solution owes its poor activity to the formation of low-soluble or essentially insoluble soaps, which prevent the concerned tissues from being penetrated and hence demolished.

The mixtures of organic solvents did even not overcome the screening step: in fact, they cause a collapsing of the tissue, which gets dehydrated and deprived of their lipidic contents. Although such an outcome can actually make it easier for the pulp to be removed by mechanical action by means of the nerve extractor, such an action is completely useless, if not even noxius, for the purposes of pulp colliquation.

The capability of dissolving dentinal pulp shown by potassium hydroxide solution was further checked by means of in vitro tests which were carried out first on animal teeth, then on human teeth available after tooth extractions. The results obtained from the tests already carried out in vitro on test tissues were widely confirmed; not only: thanks to the lower amount of material to be dissolved, the concentration could be reduced, or, with the concentration being the same, the times of treatment of pulpar cavity could be decreased. Also very interesting was the observation that the vascular tissue existing at the root apex shows a much higher resistance to hydrolysis than pulp tissue contained inside the root canal. The latter fact assures the reduced possibility of liquid penetrating under the root apex, except for extremely long treatment times which are nonetheless disadvantageous as compared to the traditional mechanical methodology. Furthermore, tests were additionally carried out on composite solutions, in which a suitable surfactant was associated with the active substance, which surfactant was so selected as not to interfere with the main action. However, the results from such tests did not show any significant differences relatively to simple solutions.

The modality of use of the product according to the present invention is extremely simple, and said use takes place as follows.

After preparing a shield around the concerned tooth with a silicone impression paste, or another suitable waterproof material, so as to prevent any leakage of the treatment liquid to take place except through a suitable drain leading to the outside of a patient's mouth (a hypodermic needle or, better, a phleboclysis drain), the solution is fed to the cavity by means of a syringe, or a phleboclysis system, or an automatic device. After a contact time, which can be comprised within the range of from 5 to 10 minutes, according to the number and the presumable diameter of the root canals to be treated, the treated area is washed with physiologic solution complying with Official Pharmacopoeia's prescriptions and is possibly dried. The root canals are then filled with the presently used stopping pastes. Like all solutions of caustic alkalies, potassium hydroxide solutions rapidly absorb carbon dioxide from atmosphere, turning into carbonate solutions. In case of multi-dose containers, this property can lead to a serious decrease in solution activity, with noxious effects on the results of tooth root canal cure treatment. However, this problem is easily solved by using pierceable stoppers of the same type as the stoppers used for the vials for injectable physiologic solution. In order to draw the solution, a needle having a suitable diameter will suffice. Once the needle is withdrawn from the stopper, the self-sealing stopper will leave the vial still tightly sealed, exactly as it occurs in the case of physiologic solution.

We claim:

1. A method of treating pulp of a tooth root canal comprising the step of treating the tooth pulp with potassium hydroxide.

2. The pulp treatment method as defined in claim 1 wherein the potassium hydroxide is in liquid solution with water.

3. The method as defined in claim 2 wherein the tooth pulp is treated with potassium hydroxide for a period of time less than 10 minutes.

4. The method as defined in claim 2 wherein the tooth pulp is treated with potassium hydroxide for a period of time less than 10 minutes, and thereafter washing the treated area.

5. The pulp treatment method as defined in claim 1 wherein the potassium hydroxide is in substantially a 20% concentration of a liquid solution with water.

6. The method as defined in claim 5 wherein the tooth pulp is treated with potassium hydroxide for a period of time less than 10 minutes.

7. The method as defined in claim 5 wherein the tooth pulp is treated with potassium hydroxide for a period of time less than 10 minutes, and thereafter washing the treated area.

8. The method as defined in claim 1 wherein the tooth pulp is treated with potassium hydroxide for a period of time less than 10 minutes.

9. The method as defined in claim 1 wherein the tooth pulp is treated with potassium hydroxide for a period of time less than 10 minutes, and thereafter washing the treated area.

10. The pulp treatment method as defined in claim 1 including the further steps of exposing the root canal of the tooth which is to be treated, and shielding soft tissue areas adjacent the tooth to be treated to prevent injury thereto.

* * * * *